US012564607B2

(12) United States Patent
Umeda et al.

(10) Patent No.: US 12,564,607 B2
(45) Date of Patent: Mar. 3, 2026

(54) CELL POPULATION COMPRISING MESENCHYMAL CELLS, PHARMACEUTICAL COMPOSITION COMPRISING THE SAME, AND METHOD FOR PRODUCING THE SAME

(71) Applicant: KANEKA CORPORATION, Osaka (JP)

(72) Inventors: Nobuyoshi Umeda, Kobe (JP); Kohei Ogura, Kobe (JP)

(73) Assignee: KANEKA CORPORATION, Osaska (JP)

( * ) Notice: Subject to any disclaimer, the term of this patent is extended or adjusted under 35 U.S.C. 154(b) by 1004 days.

(21) Appl. No.: 17/618,636

(22) PCT Filed: Jun. 12, 2020

(86) PCT No.: PCT/JP2020/023208
§ 371 (c)(1),
(2) Date: Dec. 13, 2021

(87) PCT Pub. No.: WO2020/251020
PCT Pub. Date: Dec. 17, 2020

(65) Prior Publication Data
US 2022/0233600 A1 Jul. 28, 2022

(30) Foreign Application Priority Data

Jun. 14, 2019 (JP) ................................. 2019-111470

(51) Int. Cl.
*A61K 35/28* (2015.01)
*A61P 19/02* (2006.01)
(Continued)

(52) U.S. Cl.
CPC .............. *A61K 35/28* (2013.01); *A61P 19/02* (2018.01); *A61P 29/00* (2018.01); *A61P 37/06* (2018.01)

(58) Field of Classification Search
None
See application file for complete search history.

(56) References Cited

U.S. PATENT DOCUMENTS

2003/0036196 A1 2/2003 Okano et al.
2011/0274663 A1 11/2011 Shirono et al.
(Continued)

FOREIGN PATENT DOCUMENTS

JP 5394932 B2 1/2014
JP 2015-61520 A 4/2015
(Continued)

OTHER PUBLICATIONS

Qadan MA, Piuzzi NS, Boehm C, Bova W, Moos M Jr, Midura RJ, Hascall VC, Malcuit C, Muschler GF. Variation in primary and culture-expanded cells derived from connective tissue progenitors in human bone marrow space, bone trabecular surface and adipose tissue. Cytotherapy. Mar. 2018;20(3):343-360. (Year: 2018).*
(Continued)

*Primary Examiner* — Evelyn Y Pyla
*Assistant Examiner* — Jagamya Vijayaraghavan
(74) *Attorney, Agent, or Firm* — Birch, Stewart, Kolasch & Birch, LLP

(57) ABSTRACT
This invention provides a cell population comprising mesenchymal cells capable of forming a cell sheet that can be spontaneously detached from a substrate. In such cell population comprising mesenchymal cells, the proportion of cells positive for CD324 is 70% or more and the proportion of mesenchymal cells positive for CD90 is 90% or more.

2 Claims, 4 Drawing Sheets

(51) Int. Cl.
  *A61P 29/00*          (2006.01)
  *A61P 37/06*          (2006.01)

(56)                    References Cited

U.S. PATENT DOCUMENTS

| | | |
|---|---|---|
| 2016/0228474 A1 | 8/2016 | Yamahara et al. |
| 2019/0343892 A1 | 11/2019 | Yamahara et al. |
| 2020/0040305 A1 | 2/2020 | Ino et al. |

FOREIGN PATENT DOCUMENTS

| | | |
|---|---|---|
| JP | 2019-80580 A | 5/2019 |
| WO | WO 01/68799 A1 | 9/2001 |
| WO | WO 2018/186421 A1 | 10/2018 |

OTHER PUBLICATIONS

Centurione L, Passaretta F, Centurione MA, Munari S, Vertua E, Silini A, Liberati M, Parolini O, Di Pietro R. Mapping of the Human Placenta: Experimental Evidence of Amniotic Epithelial Cell Heterogeneity. Cell Transplant. Jan. 2018;27(1):12-22. doi: 10.1177/0963689717725078. PMID: 29562779 (Year: 2018).*

Crespo-Diaz R, Behfar A, et al. Platelet lysate consisting of a natural repair proteome supports human mesenchymal stem cell proliferation and chromosomal stability. Cell Transplant. 2011;20(6):797-811. doi: 10.3727/096368910X543376. Epub Nov. 19, 2010. PMID: 21092406. (Year: 2010).*

International Search Report, issued in PCT/JP2020/023208, PCT/ISA/210, dated Jul. 21, 2020.

Written Opinion of the International Searching Authority, issued in PCT/JP2020/023208, PCT/ISA/237, dated Jul. 21, 2020.

Extended European Search Report for European Application No. 20823307.2, dated May 23, 2023.

Lee et al., "Spherical Bullet Formation via E-cadherin Promotes Therapeutic Potency of Mesenchymal Stem Cells Derived From Human Umbilical Cord Blood for Myocardial Infarction," Molecular Therapy, vol. 20, No. 7, Jul. 2012, pp. 1424-1433, XP93045402A, with Supplementary Figure S1.

* cited by examiner

CELL POPULATION COMPRISING MESENCHYMAL CELLS, PHARMACEUTICAL COMPOSITION COMPRISING THE SAME, AND METHOD FOR PRODUCING THE SAME

TECHNICAL FIELD

The present invention relates to a cell population comprising mesenchymal cells, a pharmaceutical composition comprising the cell population, and a method for producing the cell population that can be used in medical, biochemical, and other fields.

BACKGROUND ART

In regenerative therapies, cells, such as stem cells, that have been artificially cultured ex vivo are administered into the patient's body to regenerate damaged organs or tissues and recover functions. In recent years, use of novel therapy techniques comprising administering cells, such as mesenchymal stem cells, skeletal myoblasts, and epithelial cells, to patients to accelerate regeneration of tissues or organs or improved functions has advanced rapidly. For example, bone marrow-derived mesenchymal stem cell preparations targeting patients of acute graft versus host disease (GVHD), or spinal cord injury and skeletal myoblast sheets targeting patients of severe cardiac failure are commercialized in Japan as regenerative medical products.

Most cells used for regenerative therapies or other purposes adhere to a culture substrate. When producing the cell preparations described above, accordingly, it is necessary that cells be adhered to a culture substrate and cultured to grow thereon and the cells be then detached from the culture substrate. The bone marrow-derived mesenchymal stem cells described above also adhere to a culture substrate. Thus, the bone marrow-derived mesenchymal stem cells are cultured to grow while being adhered to a culture substrate, the cells are detached from the culture substrate, and a cell suspension is then recovered. The cells can be detached from a culture substrate by, for example, a chemical means involving using a protease such as trypsin or a chemical product and a physical means involving using equipment for physically detaching cells, such as a cell scraper. For example, Patent Document 1 discloses a method comprising adding trypsin to a culture substrate to detach mesenchymal stem cells.

Patent Document 2 discloses a method of using a culture substrate covered, on its surface, with temperature-reactive polymers having cell-adhesive properties that vary depending on temperatures to detach cells from the culture substrate depending on temperature changes.

PRIOR ART DOCUMENTS

Patent Documents

Patent Document 1: JP Patent 5,394,932
Patent Document 2: WO 2001/068799

SUMMARY OF THE INVENTION

Objects to Be Attained by the Invention

As described above, various techniques for detaching adhesive cells such as mesenchymal stem cells from culture substrates have been developed. According to the method of Patent Document 1, however, cultured cells are damaged by chemical substances such as trypsin. When cultured cells are detached from culture substrates via trypsin treatment, in addition, the detached cells are separated from each other to single cells, and it is impossible to detach the cells in the form of a cell sheet.

According to the method of Patent document 2, it is necessary to use a particular material as a culture substrate that serves as a cell culture scaffold. This increases a production cost, disadvantageously.

Under the above circumstances, it is an object of the present invention to provide a cell population that can be spontaneously detached from a culture substrate without the use of a chemical means, a physical means, or a special culture substrate, a method for producing the same, and a pharmaceutical composition comprising the same.

Means for Attaining the Objects

The present inventors have conducted studies in order to attain the above objects. As a result, they discovered that a cell population comprising mesenchymal cells in which the proportion of cells positive for CD324 is 70% or more and the proportion of mesenchymal cells positive for CD90 is 90% or more would be spontaneously detached from a substrate without a special means or equipment. The present invention has been completed based on such finding.

Specifically, the present invention is as follows.

(1) A cell population comprising mesenchymal cells, wherein the proportion of cells positive for CD324 is 70% or more and the proportion of mesenchymal cells positive for CD90 is 90% or more.

(2) The cell population according to (1), wherein the proportion of cells positive for CD326 is 10% or less.

(3) The cell population according to (1) or (2), wherein the proportion of mesenchymal cells positive for CD73 is 80% or more, the proportion of mesenchymal cells positive for CD166 is 80% or more, the proportion of cells positive for CD45 is 10% or less, and the proportion of mesenchymal cells positive for CD105 is 70% or more.

(4) The cell population according to any of (1) to (3), wherein the mesenchymal cells are derived from a fetal appendage.

(5) A method for producing a cell population comprising mesenchymal cells comprising:

a step of culturing of a cell population comprising mesenchymal cells; and a step of selecting a cell population having the properties (a) and (b) below from among the cell populations comprising mesenchymal cells:

(a) a cell population in which the proportion of cells positive for CD324 is 70% or more; and (b) a cell population in which the proportion of mesenchymal cells positive for CD90 is 90% or more.

(6) A pharmaceutical composition comprising the cell population according to any of (1) to (4) and a pharmaceutically acceptable medium.

(7) The pharmaceutical composition according to (6), wherein the composition is for administration to a human at a dose of $10^{12}$ or less of mesenchymal cells per one administration.

(8) The pharmaceutical composition according to (6) or (7), wherein the pharmaceutical composition is a preparation for injection.

(9) The pharmaceutical composition according to (6) or (7), wherein the pharmaceutical composition is a preparation for transplantation in the form of a cell aggregate or a sheet-like construct.

(10) The pharmaceutical composition according to any of (6) to (9), wherein the composition is a medicament for use in the treatment of a disease selected from among immune-related disease, ischemic disease, lower limb ischemia, cerebral vascular ischemia, renal ischemia, pulmonary ischemia, neurological disease, graft-versus-host disease, inflammatory bowel disease, Crohn's disease, ulcerative colitis, radiation enteritis, systemic erythematosus, lupus erythematosus, collagen disease, stroke, cerebral infarction, cerebral hematoma, cerebrovascular paralysis, cerebral tumor, cirrhosis, atopic dermatitis, multiple sclerosis, psoriasis, bullous epidermolysis, diabetes, mycosis fungoides, scleroderma, diseases resulting from degeneration and/or inflammation of connective tissues such as cartilage, articular cartilage defects, meniscal damage, osteochondrosis detachment, indestructible osteonecrosis, knee osteoarthritis, inflammatory arthritis, rheumatoid arthritis, eye disease, angiogenesis-related disease, ischemic heart disease, coronary heart disease, myocardial infarction, angina, heart failure, cardiomyopathy, valvular disease, wound, epithelial damage, fibrosis, pulmonary disease, muscular dystrophy, chronic pancreatitis, chronic nephritis, and cancer.

(11) Use of the cell population comprising mesenchymal cells according to any of (1) to (4) in the manufacture of a pharmaceutical composition.

(12) Use of the cell population comprising mesenchymal cells according to any of (1) to (4) in the manufacture of a cell therapy medicament.

(13) Use of the cell population comprising mesenchymal cells according to any of (1) to (4) in the manufacture of a medicament for regeneration of cardiac muscles, production of cardiomyocytes, angiogenesis, repair of blood vessels, or suppression of immune responses.

(14) The cell population comprising mesenchymal cells according to any of (1) to (4), for use in the treatment of a disease.

(15) The cell population according to (14), wherein the disease is any of the diseases recited in (10).

(16) The cell population comprising mesenchymal cells according to any of (1) to (4), for administration to a patient or subject for regeneration of cardiac muscles, production of cardiomyocytes, angiogenesis, repair of blood vessels, or suppression of immune responses.

(17) A method for treating a disease in a patient or subject comprising a step of administering a therapeutically effective amount of the cell population comprising mesenchymal cells according to any of (1) to (4) to the patient or subject.

(18) The method according to (17), wherein the disease is any of the diseases recited in (10) and the patient or subject is in need of treatment of the disease.

(19) The method according to (17) or (18), wherein the patient is a human and the single dose is $10^{12}$ cells or less.

(20) The method according to (17), (18), or (19), wherein the cell population is in the form of a cell aggregate or a sheet-like construct.

(21) A method of performing regeneration of cardiac muscles, production of cardiomyocytes, angiogenesis, repair of blood vessels, or suppression of immune responses in a patient or subject comprising a step of administering a therapeutically effective amount of the cell population comprising mesenchymal cells according to any of (1) to (4) to a patient or subject.

(22) The method according to (21), wherein the patient is a human and the single dose is $10^{12}$ cells or less.

(23) The method according to (21) or (22), wherein the cell population in the form of a cell aggregate or a sheet-like construct.

This description incorporates part or all of the content as disclosed in the description and/or drawings of Japanese Patent Application No. 2019-111470, which is a priority document of the present application.

Effects of the Invention

The cell population according to one or more embodiments of the present invention can be spontaneously detached from a culture substrate without the use of a chemical means and/or physical means.

According to the method for production of the cell population according to one or more embodiments of the present invention, a cell population exerting the effects described above can be produced efficiently.

The pharmaceutical composition according to one or more embodiments of the present invention can be used for treatment of immune-related diseases and other diseases.

EMBODIMENTS OF THE INVENTION

[1] Explanation of Terms

Figure 1:
FIG. 1 shows an image of cells 21 days after initiation of the 5th passage culture of the cell population of Comparative Example 1 prepared from Donor #1 observed in Evaluation 1 (magnification: 40).

The term "mesenchymal cells" used herein refers to cells that show at least one property selected from among CD73 positivity, CD90 positivity, CD166 positivity, CD105 positivity, CD45 negativity, and CD326 negativity. Typically, the "mesenchymal cells" have the properties i) and ii) below. "Mesenchymal stromal cells" and "mesenchymal stem cells (MSC)" are within the scope of the mesenchymal cells in the present invention.

As the "mesenchymal cells," cells that show at least one property selected from among CD73 positivity, CD90 positivity, CD166 positivity, CD105 positivity, CD45 negativity, and CD326 negativity selected from among somatic cells (tissue cells) that can be sampled from various tissues and organs can be used. Preferably, cells having the properties i) and ii) described below can be used. Examples of the somatic cells include, but are not particularly limited to, fat cells, fat stem cells, neural cells, neural stem cells, cardiac muscle cells, cardiac muscle stem cells, hepatic cells, hepatic stem cells, epithelial cells, epithelial stem cells, skeletal muscle cells, skeletal muscle stem cells, hematopoietic cells, hematopoietic stem cells, mesenchymal cells, mesenchymal stem cells, mesenchymal cells derived from the amniotic membrane, mesenchymal stem cells derived from the amniotic membrane, mesenchymal cells derived from the amniotic epithelium, mesenchymal stem cells derived from the amniotic epithelium, mesenchymal cells derived from the extracellular matrix layer of the amniotic membrane, mesenchymal stem cells derived from the extracellular matrix layer of the amniotic membrane, gastrointestinal epithelial cells, gastrointestinal epithelial stem cells, osteoblasts, cartilage cells, synovial cells, and synovial stem cells.

Typical Properties of Mesenchymal Cells in the Present Invention i) The mesenchymal cells are adhesive to plastic materials under culture conditions in a standard medium. The term "standard medium" used herein refers to a medium comprising a basal medium (e.g., αMEM medium) supplemented with serum, a serum replacement reagent, or a growth factor (e.g., a human platelet lysate as a serum replacement reagent).

ii) The mesenchymal cells are positive for surface antigens CD73 and CD90 and negative for CD45 and CD326.

The "mesenchymal cells" may show at least one property selected from among CD73 positivity, CD90 positivity, CD166 positivity, CD105 positivity, CD45 negativity, and CD326 negativity. For example, such cells can be positive for CD73, positive for CD90, negative for CD45, and negative for CD326. Whether or not such cells are capable of differentiating into bone, cartilage, fat, and other cells is not particularly limited. The "mesenchymal cells" encompass cells that can differentiate into bone, cartilage, and fat cells as mesenchymal stem cells. The "mesenchymal cells" also encompass cells that are positive for CD73, positive for CD90, positive for CD166, positive for CD105, negative for CD45, or negative for CD326 but are not capable of differentiating into bone, cartilage, and fat cells. Further, the "mesenchymal cells" encompass cells that are positive for CD73, positive for CD90, positive for CD166, positive for CD105, negative for CD45, or negative for CD326 and are capable of differentiating selectively into one or two of bone, cartilage, and fat cells.

The term "fetal appendage" as used herein refers to fetal membrane, placenta, umbilical cord, and amniotic fluid. Furthermore, the "fetal membrane" is a fetal sac containing fetal amniotic fluid, which consists of an amniotic membrane, a chorion membrane, and a decidual membrane in this order from the inside. Among them, an amniotic membrane and a chorion membrane are originated from the fetus. The "amniotic membrane" refers to a transparent thin membrane that is present in the innermost layer of the fetal membrane and poor in blood vessels, and the inner wall is covered with a layer of epithelial cells with secretory function to secrete amniotic fluid. The inner layer of the amniotic membrane (also referred to as "the epithelial cell layer") is covered with a layer of epithelial cells with secretory function to secrete amniotic fluid, and the outer layer of the amniotic membrane (also referred to as "the extracellular matrix layer," which corresponds to the interstitium) comprises mesenchymal cells.

The "cell population comprising mesenchymal cells" as used herein is not particularly limited in terms of its state. Examples thereof include cell pellets, cell aggregates, cell sheets, suspended cells, cell suspensions, and frozen products of any thereof.

The term "the proportion of (mesenchymal) cells that are positive for" a particular surface antigen refers to, as described in the examples below, the proportion of cells that are positive for a particular surface antigen in a target cell population analyzed via flow cytometry. The proportion of cells that are positive for a particular surface antigen may be referred to as a "positive rate" herein, and the proportion of cells that are negative for a particular surface antigen may be referred to as a "negative rate" herein.

The proportion of particular cells in a cell population is a proportion of the number of the particular cells relative to the total number of cells constituting a target cell population.

The mesenchymal cells, the cell population comprising mesenchymal cells, and the fetal appendages are preferably derived from humans.

[2] A Cell Population Comprising Mesenchymal Cells

The cell population according to one or more embodiments of the present invention is a cell population comprising mesenchymal cells, wherein the proportion of cells that are positive for CD324 is 70% or more, and the proportion of mesenchymal cells that are positive for CD90 is 90% or more. The cells that are positive for CD324 may be mesenchymal cells.

When a cell population comprising mesenchymal cells having the properties as described above is cultured on a substrate, the cell population comprising mesenchymal cells is spontaneously detached from the substrate without a general chemical and/or physical means. In a preferable embodiment, the cell population comprising mesenchymal cells is spontaneously detached from the substrate in the form of a cell sheet.

The "cell population comprising mesenchymal cells" used herein is not particularly limited, provided that it comprises mesenchymal cells at least, and it may comprise other cells. While the proportion of mesenchymal cells in the cell population comprising mesenchymal cells is not particularly limited, it may be 70% or more, 75% or more, 80% or more, 85% or more, 87% or more, 88% or more, 89% or more, 90% or more, 91% or more, 92% or more, 93% or more, 94% or more, 95% or more, 97% or more, 99% or more, or 100%.

The proportion of other cells in the cell population comprising mesenchymal cells may be 30% or less, 20% or less, 10% or less, 5% or less, 3% or less, 1% or less, or 0%. The other cells are not particularly limited, provided that such cells are other than the mesenchymal cells. For example, the other cells may be blood cells, such as lymphocytes, granulocytes, or erythrocytes.

CD324 as a surface antigen is a cluster of differentiation 324, which is a protein also known as an epithelial cadherin (E-cadherin).

CD90 as a surface antigen is a cluster of differentiation 90, which is a protein also known as Thy-1.

In the cell population, the proportion of cells that are positive for CD324 is more preferably 75% or more, 80% or more, 85% or more, 87% or more, 88% or more, 89% or more, 90% or more, 91% or more, 92% or more, 93% or more, 94% or more, or 95% or more.

The proportion of mesenchymal cells that are positive for CD90 in the cell population is more preferably 91% or more, 92% or more, 93% or more, 94% or more, 95% or more, 96% or more, 97% or more, 98% or more, 99% or more, or 100%.

In the cell population according to one or more embodiments of the present invention, the proportion of cells that are positive for CD326 is preferably 10% or less.

CD326 is a cluster of differentiation 326, which is a protein also known as EpCAM.

The proportion of mesenchymal cells that are positive for CD326 in the cell population is more preferably 5% or less (negative rate: 95% or more), 4% or less (negative rate: 96% or more), 3% or less (negative rate: 97% or more), 2% or less (negative rate: 98% or more), 1% or less (negative rate: 99% or more), or 0% (negative rate: 100%).

The cell population comprising mesenchymal cells according to an embodiment of the present invention preferably satisfies at least one of the following conditions and more preferably satisfies all of the following conditions: the proportion of mesenchymal cells that are positive for CD73 is 90% or more; the proportion of mesenchymal cells that are positive for CD166 is 80% or more; the proportion of mesenchymal cells that are positive for CD105 is 70% or more; and the proportion of cells that are positive for CD45 is 10% or less. In the cell population comprising mesenchymal cells according to an embodiment of the present invention, it is preferable that the proportion of cells that are positive for CD34 be 10% or less.

CD73 is a cluster of differentiation 73, which is a protein also known as 5-nucleotidase or ecto-5'-nucleotidase.

CD166 is a cluster of differentiation 166, which is a protein also known as an activated leukocyte cell adhesion molecule (ALCAM).

CD105 is a cluster of differentiation 105, which is a protein also known as endoglin.

CD45 is a cluster of differentiation 45, which is a protein also known as a protein tyrosine phosphatase, receptor type, C (PTPRC) or a leukocyte common antigen (LCA).

CD34 is a cluster of differentiation 34, which is a protein also known as a hematopoietic progenitor cell antigen CD34.

The proportion of mesenchymal cells that are positive for CD73 in the cell population is more preferably 91% or more, 92% or more, 93% or more, 94% or more, 95% or more, 96% or more, 97% or more, 98% or more, 99% or more, or 100%.

The proportion of mesenchymal cells that are positive for CD166 in the cell population is more preferably 85% or more, 90% or more, 95% or more, 96% or more, 97% or more, 98% or more, or 99% or more.

The proportion of mesenchymal cells that are positive for CD105 in the cell population is more preferably 74% or more, 75% or more, 80% or more, 85% or more, 89% or more, 90% or more, 91% or more, 92% or more, 93% or more, 94% or more, or 95% or more.

The proportion of cells that are positive for CD45 in the cell population is more preferably 5% or less (negative rate: 95% or more), 4% or less (negative rate: 96% or more), 3% or less (negative rate: 97% or more), 2% or less (negative rate: 98% or more), 1% or less (negative rate: 99% or more), or 0% (negative rate: 100%).

The proportion of cells that are positive for CD34 in the cell population is more preferably 5% or less (negative rate: 95% or more), 4% or less (negative rate: 96% or more), 3% or less (negative rate: 97% or more), 2% or less (negative rate: 98% or more), 1% or less (negative rate: 99% or more), or 0% (negative rate: 100%).

The cells or mesenchymal cells that are positive for CD324, CD90, CD326, CD73, CD166, CD105, CD45, and CD34 are positive for the expression of CD324, CD90, CD326, CD73, CD166, CD105, CD45, and CD34, respectively.

The expression marker used as the indicator in one or more embodiments of the present invention (CD324, CD90, CD326, CD73, CD166, CD105, CD45, or CD34) can be detected by any detection method known in the art. Examples of methods for detecting expression markers include, but are not limited to, flow cytometry and cell staining. When a cell emitting a stronger fluorescence than a negative control (isotype control) is detected via flow cytometry involving the use of a fluorescence-labeled antibody, the cell is determined to be "positive" for the marker. Any fluorescence-labeled antibody known in the art can be used. Examples thereof include, but are not limited to, antibodies labeled with fluorescein isothiocyanate (FITC), phycoerythrin (PE), and allophycocyanin (APC). When cells that are colored or fluorescent are observed under a microscope in cell staining, the cell is determined to be "positive" for the marker. Cell staining may be immune cell staining using antibodies or non-immune cell staining without using antibodies. Antibodies used in immune cell staining are not particularly limited, antibodies that are generally used to detect markers of interest can be used, and the antibodies used in the examples described below are preferably used. For example, antibodies used for detecting cells that are positive for CD324 are not particularly limited, and cells that are positive for CD324 can be detected using antibodies prepared from REA811, 67A4, and SPM381 clones. In one or more embodiments of the present invention, cells that are positive for CD324 are more preferably detected using antibodies prepared from REA811 clones. The term "expression marker" is synonymous with the term "surface antigen," and these terms are interchangeable.

Whether or not the cell population according to one or more embodiments of the present invention has the capacity of differentiation is not particularly limited. It is preferable that the cell population have the capacity of differentiation into cartilage tissue and that it have no or low capacity of differentiation into fat tissue. It is more preferable that the cell population have no or low capacity of differentiation into bone tissue.

The cell population according to one or more embodiments of the present invention can be stored in a frozen state until immediately before use. The cell population may contain any components, in addition to mesenchymal cells and other cells. Examples of such components include, but are not limited to, salts, polysaccharides (e.g., HES and dextran), proteins (e.g., albumin), DMSO, and medium components (e.g., components contained in RPMI 1640 medium).

[3] A Method for Producing a Cell Population Comprising Mesenchymal Cells

The method for producing a cell population comprising mesenchymal cells according to one or more embodiments of the present invention comprises: a step of culturing a cell population comprising mesenchymal cells; and a step of selecting a cell population having the properties (a) and (b) below from among the cell populations comprising mesenchymal cells: (a) a cell population in which the proportion of cells that are positive for CD324 is 70% or more; and (b) a cell population in which the proportion of mesenchymal cells that are positive for CD90 is 90% or more.

According to the method for producing a cell population comprising mesenchymal cells according to one or more embodiments of the present invention, a cell population comprising mesenchymal cells having the properties (a) and (b) above can be produced. Such properties are useful as indicators when obtaining a cell population comprising mesenchymal cells that can be spontaneously detached from a substrate. Such properties are also useful as indicators when obtaining the detached mesenchymal cell population in the form of a cell sheet instead of single cells.

In the method for producing the cell population, the step of culturing a cell population comprising mesenchymal cells may be carried out separately from the step of selecting a cell population having the properties described above from among the cell populations comprising mesenchymal cells. Alternatively, the step of culturing may be integral with the step of selection. For example, a cell population comprising mesenchymal cells may be cultured under particular conditions in which a cell population that has either or both the properties (a) and (b) can be selected, as described below. Thus, the step of culturing can be integral with the step of selection.

In the method for producing a cell population, a step of selecting a cell population that has the properties is not particularly limited, provided that a cell population that has the properties can be selected. In such a step, for example, a cell population that has the property (a) is selected using a cell sorter, and the selected cell population is then cultured under conditions in which a cell population that has the property (b) can be selected. Alternatively, a cell population that has the property (b) may be selected using a cell sorter, and the selected cell population may then be cultured under conditions in which a cell population that has the property (a) can be selected. According to another method for producing a cell population that has the properties, a cell population may be cultured under particular conditions in which a cell population that has the properties (a) and (b) can be selected. Culture conditions and culture methods are described in detail below. Also, a cell population that has the properties can be selected by the method described with regard to the method for selecting a cell population described below.

The method for producing a cell population comprising mesenchymal cells according to one or more embodiments of the present invention may further comprise a step of obtaining a cell population comprising subjecting fetal appendages, such as amniotic membrane, to an enzyme treatment to obtain a cell population comprising mesenchymal cells as a starting material.

The amniotic membrane consists of an epithelial cell layer and an extracellular matrix layer, and the latter contains mesenchymal cells. The step of obtaining a cell population may further comprise a step of obtaining an amniotic membrane by caesarean section.

The cell population containing cells sampled from a fetal appendage is preferably a cell population obtained by treating a sample containing an epithelial cell layer and an extracellular matrix layer containing mesenchymal cells sampled from the fetal appendages at least with collagenase.

When a sample obtained from fetal appendages (preferably a sample containing an epithelial cell layer and an extracellular matrix layer containing mesenchymal cells) is subjected to an enzyme treatment, the mesenchymal cells contained in the extracellular matrix layer of the fetal appendages are preferably released, and such enzyme treatment is carried out with the use of an enzyme that does not degrade the epithelial cell layer (or a combination thereof). Such enzyme is not particularly limited, and examples thereof include collagenase and/or metalloproteinase. Examples of the metalloproteinase include, but are not limited to, thermolysin and/or dispase as a metalloproteinase cleaving the N-terminal side of the nonpolar amino acid.

The activity concentration of collagenase is preferably 50 PU/ml or more, more preferably 100 PU/ml or more, and further preferably 200 PU/ml or more. While the activity concentration of collagenase is not particularly limited, it is, for example, 1000 PU/ml or less, 900 PU/ml or less, 800 PU/ml or less, 700 PU/ml or less, 600 PU/ml or less, or 500 PU/ml or less. PU (protease unit) is defined as the amount of enzyme that degrades 1 μg of FITC-collagen in 1 minute at pH 7.5 and 30° C.

The activity concentration of metalloproteinase (e.g., thermolysin and/or dispase) is preferably 50 PU/ml or more, more preferably 100 PU/ml or more, further preferably 150 PU/ml or more, and still further preferably 190 PU/ml or more. The activity concentration of metalloproteinase is preferably 1000 PU/ml or less, more preferably 900 PU/ml or less, further preferably 800 PU/ml or less, further preferably 700 PU/ml or less, further preferably 600 PU/ml or less, further preferably 500 PU/ml or less, and further preferably 300 PU/ml or less. In an embodiment in which dispase is used as metalloproteinase, PU (protease unit) is defined as the amount of enzyme that releases 1 μg of tyrosine-equivalent amino acid from lactic casein in 1 minute at pH 7.5 at 30° C. The mesenchymal cells contained in the extracellular matrix layer can be efficiently released while preventing the contamination of epithelial cells contained in the epithelial cell layer of the fetal appendages within the above enzyme concentration range. A preferable combination of concentrations of collagenase and/or metalloproteinase can be determined by microscopic observation of fetal appendages after enzyme treatment and flow cytometry of the obtained cells.

From the viewpoint of efficient recovery of living cells, it is preferable to treat fetal appendages using collagenase in combination with metalloproteinase. It is more preferable to simultaneously treat fetal appendages using collagenase in combination with metalloproteinase. In such a case, thermolysin and/or dispase can be used as the metalloproteinase, although the enzymes are not limited thereto. Mesenchymal cells can be readily obtained by treating fetal appendages only once using an enzyme solution containing collagenase and metalloproteinase. In addition, it is possible to reduce the risk of contamination with bacteria, viruses, or other substances by simultaneously treating the fetal appendages.

It is preferable that fetal appendages be subjected to enzyme treatment by immersing the amniotic membrane in an enzyme solution with stirring via a stirring means, after washing the membrane with a wash solution, such as physiological saline or a Hank's balanced salt solution. As such stirring means, for example, a stirrer or a shaker can be used from the viewpoint of efficient release of the mesenchymal cells contained in the extracellular matrix layer of the fetal appendage, although the stirring means is not limited thereto. The stirring speed is not particularly limited. When a stirrer or shaker is used, it is, for example, 5 rpm or higher, 10 rpm or higher, 20 rpm or higher, 30 rpm or higher, 40 rpm or higher, or 50 rpm or higher. The stirring speed is not particularly limited. When a stirrer or a shaker is used, it is, for example, 100 rpm or lower, 90 rpm or lower, 80 rpm or lower, 70 rpm or lower, or 60 rpm or lower. The enzyme treatment period is not particularly limited, and it is, for example, 10 minutes or longer, 20 minutes or longer, 30 minutes or longer, 40 minutes or longer, 50 minutes or longer, 60 minutes or longer, 70 minutes or longer, 80 minutes or longer, or 90 minutes or longer. The enzyme treatment period is not particularly limited, and it is, for example, 6 hours or shorter, 5 hours or shorter, 4 hours or shorter, 3 hours or shorter, 2 hours or shorter, 110 minutes or shorter, or 100 minutes or shorter. The enzyme treatment temperature is not particularly limited, and it is, for example, 15° C. or higher, 16° C. or higher, 17° C. or higher, 18° C. or higher, 19° C. or higher, 20° C. or higher, 21° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, 35° C. or higher, or 36° C. or higher. The enzyme treatment temperature is not particularly limited, and it is, for example, 40° C. or lower, 39° C. or lower, 38° C. or lower, or 37° C. or lower.

In the method of production according to one or more embodiments of the present invention, it is possible to separate and/or recover the released mesenchymal cells from an enzyme solution containing the released mesenchymal cells in accordance with a conventional technique involving the use of, for example, a filter, a centrifuge, a hollow fiber separation membrane, or a cell sorter. It is preferable that an enzyme solution containing the released mesenchymal cells be filtrated through a filter. In an embodiment in which the enzyme solution is filtrated through a filter, the released cells selectively pass through a filter, and the undegraded epithelial cell layer cannot pass through the filter and remains on the filter. Thus, the released mesenchymal cells can be separated and/or recovered easily, and the risk of contamination with bacteria, viruses, and other substances can be reduced. An example of a filter is, but is not particularly limited to, a mesh filter. The pore size (mesh size) of the mesh filter is not particularly limited, and it is, for example, 40 μm or greater, 50 μm or greater, 60 μm or greater, 70 μm or greater, 80 μm or greater, or 90 μm or greater. The pore size of the mesh filter is not particularly limited, and it is, for example, 200 μm or smaller, 190 μm or smaller, 180 μm or smaller, 170 μm or smaller, 160 μm or smaller, 150 μm or smaller, 140 μm or smaller, 130 μm or smaller, 120 μm or smaller, 110 μm or smaller, or 100 μm or smaller. The filtration speed is not particularly limited. The pore size of the mesh filter may be adjusted within the above range, so that the enzyme solution containing mesenchymal cells can be filtrated by free fall, and it is possible to prevent the cell viability from lowering.

Nylon is preferably used as a material for the mesh filter. A tube containing a 40 μm, 70 μm, 95 μm, or 100 μm nylon mesh filter such as a Falcon cell strainer, which is widely used for research purposes, can be used. Alternatively, medical mesh cloth (nylon and polyester) used for hemodialysis and the like can be used. Further, an arterial filter used for extracorporeal circulation (a polyester mesh filter; pore size: 40 μm to 120 μm) can be used. A mesh filter made of any other material, such as a stainless-steel mesh filter, can also be used.

It is preferable that the mesenchymal cells be allowed to pass through a filter by natural drop (free fall). It is also possible to force the cells to pass through a filter by suction using a pump or other means. In such a case, it is preferable that a pressure be made as small as possible to avoid damage of the cells.

A cell population comprising mesenchymal stem cells that has passed through the filter can be recovered by centrifugation after dilution of the filtrate with at least two times its volume of a medium or balanced salt buffer solution. Examples of the balanced salt buffer solution that can be used include, but are not limited to, Dulbecco's phosphate buffer (DPBS), Earle's balanced salt solution (EBSS), Hank's balanced salt solution (HBSS), and phosphate buffer (PBS).

The method of production according to one or more embodiments of the present invention comprises a step of culturing a cell population comprising mesenchymal cells.

In the step of culturing a cell population comprising mesenchymal cells, the cell seeding density is not particularly limited. For example, cells can be seeded at a density of 500 to 10,000 cells/cm$^2$. The lower limit of the seeding density is preferably, for example, 500 cells/cm$^2$, 1,000 cells/cm$^2$, 2000 cells/cm$^2$, 3,000 cells/cm$^2$, 4,000 cells/cm$^2$, or 5,000 cells/cm$^2$. The upper limit of the seeding density is preferably, for example, 10,000 cells/cm$^2$, 9,000 cells/cm$^2$, 8,000 cells/cm$^2$, or 7,000 cells/cm$^2$.

The step of culturing may comprise a step of passage culture or it may comprise a step of conducting a plurality of stages of culturing under different culture conditions.

A period of culturing for a single passage or stage can be, for example, 4 to 10 days. More specifically, it can be 4 days, 5 days, 6 days, 7 days, 8 days, 9 days, or 10 days.

The medium for use in the culture can be prepared by utilizing any liquid medium for animal cell culture as a basal medium and, if necessary, appropriately adding other components (serum, a serum replacement reagent, a growth factor, etc.) thereto. In an embodiment in which a growth factor is added to the basal medium, a reagent (heparin, etc.) for stabilizing the growth factor in the medium may be further added in addition to the growth factor, or the growth factor may be stabilized with a gel, a polysaccharide, or the like in advance, and the stabilized growth factor may be added to the basal medium. A medium prepared by adding serum, a serum replacement reagent, or a growth factor to a basal medium to be used for culture of a cell population comprising mesenchymal cells is defined as a standard medium.

Examples of the basal medium that can be used include, but are not particularly limited to, BME medium, BGJb medium, CMRL 1066 medium, Glasgow MEM medium, Improved MEM Zinc Option medium, IMDM medium (Iscove's Modified Dulbecco's Medium), Medium 199 medium, Eagle MEM medium, αMEM (alpha modification of Minimum Essential Medium Eagle) medium, DMEM medium (Dulbecco's Modified Eagle's Medium), Ham's F10 medium, Ham's F12 medium, RPMI 1640 medium, Fischer's medium, and a mixed medium thereof such as DMEM/F12 medium (Dulbecco's Modified Eagle's Medium/Nutrient Mixture F-12 Ham). An example of a preferable basal medium is αMEM medium.

Examples of other components to be added to the basal medium include albumin, bovine serum, a serum replacement reagent, and a growth factor, with the serum replacement reagent being preferable. As the serum replacement reagent, human platelet lysate is particularly preferable. It is particularly preferable that culturing be conducted in a basal medium that contains a serum replacement reagent but does not contain albumin, bovine serum, and a growth factor. The lower limit of the final concentration of the human platelet lysate in the medium is, for example, 1% by weight, 2% by weight, or 3% by weight. The upper limit of the concentration of the human platelet lysate in the medium is preferably, for example, 20% by weight, 10% by weight, or 7% by weight.

A commercially available serum-free medium may be used for the culture described above. Examples thereof include, but are not particularly limited to, STK 1 and STK 2 (DS Pharma Biomedical Co., Ltd.), EXPREP MSC Medium (Biomimetics Sympathies), and Corning stemgro human mesenchymal stem cell medium (Corning).

A cell population comprising mesenchymal cells can be cultured by, for example, the following steps. At the outset, the cell suspension is centrifuged, the supernatant is removed, and the obtained cell pellets are suspended in the medium. Subsequently, cells are seeded in a culture vessel (e.g., a plastic culture vessel) and cultured using a medium at 37° C. in the presence of 3% to 5% $CO_2$. The cells obtained by such culture are the cells once cultured.

The cells once cultured can further be passaged and cultured, for example, as follows. At the outset, the cells cultured to a confluency of 95% or less in the first culture are treated with ethylenediaminetetraacetic acid (EDTA) and then with trypsin, and the treated cells are detached from a culture vessel (e.g., a plastic culture vessel). The cell population produced according to one or more embodiments of the present invention can be detached from a substrate under mild conditions, and such cell population can be easily detached from a culture vessel via trypsin treatment. Thus, damages imposed on the cells via trypsin treatment can be reduced. When a cell population constitutes a cell sheet on a substrate, in addition, it is easy to detach the cell sheet from the substrate and to disintegrate the cell sheet via enzyme treatment to obtain a cell suspension. Thus, damages imposed on the cells can be reduced. Subsequently, the resulting cell suspension is centrifuged, the supernatant is removed, and the obtained cell pellets are re-suspended in the medium. In the end, cells are seeded in a culture vessel (e.g., a plastic culture vessel) and cultured using a medium at 37° C. in the presence of 3% to 5% $CO_2$. The cells obtained by such passage culture are the cells once cultured. By carrying out the same passage culture, cells passaged "n" number of times can be obtained (n is an integer of 1 or more). When performing passage culture, the cells are cultured to a confluency of 95% or less, the cells are detached and recovered in the manner described above, and the obtained cells can be used for the subsequent culture. In order to produce a large amount of cells, the lower limit of the number of passage "n" is preferably, for example, 1, 2, 3, 4, or 5. In order to suppress aging of cells, the upper limit of the number of passage "n" is preferably, for example, 50, 45, 40, 35, or 30. When the cultured cells are to be recovered without further passage culture, the cells are cultured to a confluency of 100% or more to form a cell sheet on the substrate, and culturing is further continued. Thus, the cell sheet can be spontaneously detached from the substrate.

The method of production according to one or more embodiments of the present invention may comprise a step of selecting a cell population having the properties (a) and (b) below:

(a) a cell population in which the proportion of cells that are positive for CD324 is 70% or more; and (b) a cell population in which the proportion of mesenchymal cells that are positive for CD90 is 90% or more.

As a method for selecting a cell population using the properties described above as indicators, as described above, a method comprising a step of selecting a cell population that has the properties (a) and/or (b) using a cell sorter and a step of culture under conditions in which a cell population with the properties that is not selected in the previous step can be employed, according to need. Examples of methods of selections that can be employed other than a cell sorter include FACS and a physical means, such as fractionation using magnetic beads.

As another step of selecting, a cell population may be cultured under particular conditions in which a cell population that has the properties (a) and (b) can be selected. In the step of culturing a cell population described above, for example, a cell population that has the properties (a) and (b) can be obtained by employing preferable culture conditions in adequate combinations. In such a case, a part of or the entire step of culturing a cell population may be a step of selecting a cell population that has the properties (a) and (b). For example, a cell population comprising mesenchymal cells may be cultured in a medium supplemented with a serum replacement reagent, such as a human platelet lysate. Specifically, culturing may be performed via a chemical method in which cells that do not satisfy the conditions are eliminated so that a cell population comprising mesenchymal cells satisfying the conditions is selected under adequate conditions involving, for example, culturing in a basal medium supplemented with a human platelet lysate. Alternatively, culturing may be performed by selecting an adequate standard medium, such as a basal medium supplemented with a human platelet lysate, and culturing a cell population in the medium, so that the cell population is modified to satisfy the conditions. It should be noted that the method is not limited and an adequate method may be selected in accordance with a method of culture or other conditions.

Prior to the step of selecting, a step of identifying a cell population comprising pluripotent stem cells may be performed using the properties as the indicators.

The timing of selection of a cell population having the properties (a) and (b) is not particularly limited. For example, the selection may be performed before culturing, during culturing, after culturing, before recovery of a cell population, after recovery of a cell population, before preparation of cell stocks for cryopreservation, or after thawing of the cell stocks for cryopreservation.

A method for selecting a cell population having the properties (a) and (b) is described in more detail.

An example of a method for selecting a cell population having the properties (a) and (b) via culture of a cell population is a method in which a cell population comprising mesenchymal cells is seeded on a culture substrate and cultured to grow on the culture substrate, mesenchymal cells that are positive for CD324 and CD90 are selected, and a cell population in which the proportion of cells that are positive for CD324 is 70% or more and the proportion of mesenchymal cells that are positive for CD90 is 90% or more is detached and recovered. In such a case, the culturing may be performed with the use of a culture substrate coated with the anti-CD324 antibody or anti-CD90 antibody. The timing for selection of mesenchymal cells that are positive for CD324 and CD90 from among cell populations comprising mesenchymal cells via culturing is not particularly limited, and selection can be performed during any passage culture. It is preferable that mesenchymal cells that are positive for CD324 and CD90 be selected from among cell populations comprising mesenchymal cells in the primary culture.

Alternatively, mesenchymal cells positive for CD324 and CD90 can be selected from among cell populations comprising mesenchymal cells via flow cytometry or a cell separation means involving the use of magnetic beads.

When selecting a cell population, it is preferable to select a cell population in which the proportion of cells that are positive for CD326 is 10% or less. Also, it is preferable to select a cell population that satisfies at least one and more preferably all of the following conditions: the proportion of mesenchymal cells that are positive for CD73 is 80% or more; the proportion of mesenchymal cells that are positive for CD166 is 80% or more; the proportion of mesenchymal cells that are positive for CD105 is 70% or more; and the proportion of cells that are positive for CD45 is 10% or less. Further, it is preferable to select a cell population in which the proportion of cells that are positive for CD34 is 10% or lower. The selected cell population may further be cultured in accordance with the method described above. The step of selecting a cell population having additional properties may be integral with a step of culturing a cell population, or the step of selecting may be performed separately from the s means involving using a step of culturing. The step of selecting a cell population having additional properties may be integral with the step of selecting a cell population having the properties (a) and (b), or the former step of selecting may be performed separately from the latter step of selecting.

The method of production according to one or more embodiments of the present invention can comprise a step of cryopreservation of the cell population comprising mesenchymal cells. In an embodiment comprising the step of cryopreservation of the cell population, the cell population may be thawed, and the cell population may then be separated, recovered, and/or cultured, according to need. Alternatively, the cell population may be thawed and used in that state.

Means for cryopreservation of the cell population comprising mesenchymal cells are not particularly limited. Examples thereof include a program freezer, a deep freezer, and immersion in liquid nitrogen. The temperature during freezing is preferably −30° C. or lower, −40° C. or lower, −50° C. or lower, −60° C. or lower, −70° C. or lower, −80° C. or lower, −90° C. or lower, −100° C. or lower, −110° C. or lower, −120° C. or lower, −130° C. or lower, −140° C. or lower, −150° C. or lower, −160° C. or lower, −170° C. or lower, −180° C. or lower, −190° C. or lower, or −196° C. (the temperature of liquid nitrogen) or lower. A preferable freezing speed is, for example, −1° C./min, −2° C./min, −3° C./min, −4° C./min, −5° C./min, −6° C./min, −7° C./min, −8° C./min, −9° C./min, −10° C./min, −11° C./min, −12° C./min, −13° C./min, −14° C./min, or −15° C./min. When a program freezer is used as a freezing means, for example, a temperature can be lowered to a level between −50° C. and −30° C. (e.g., −40° C.) at a freezing speed of −2° C./min to −1° C./min, and a temperature can further be lowered to a level between −100° C. and −80° C. (e.g., −90° C.) at a freezing speed of −11° C./min to −9° C./min (e.g., −10° C./min).

When freezing the cells by the freezing means described above, the cell population may be frozen in any storage container. Examples of such storage containers include, but are not limited to, cryotubes, cryovials, freezing bags, and infusion bags.

A cryopreservation solution preferably contains albumin at a predetermined concentration of more than 0% by mass, so as to enhance the viability of mesenchymal cells with a relatively high growth capacity. A preferable albumin concentration is, for example, 0.5% by mass or more, 1% by mass or more, 2% by mass or more, 3% by mass or more, 4% by mass or more, 5% by mass or more, 6% by mass or more, 7% by mass or more, or 8% by mass or more. A preferred albumin concentration is, for example, 40% by mass or less, 35% by mass or less, 30% by mass or less, 25% by mass or less, 20% by mass or less, 15% by mass or less, 10% by mass or less, or 9% by mass or less. Examples of albumin include, but are not limited to, bovine serum albumin, mouse albumin, and human albumin.

[4] Pharmaceutical Composition

The cell population comprising mesenchymal cells according to one or more embodiments of the present invention can be used as a pharmaceutical composition. According to one or more embodiments of the present invention, specifically, a pharmaceutical composition comprising the cell population and a pharmaceutically acceptable medium is provided.

The pharmaceutical composition according to one or more embodiments of the present invention can be used as a cell therapy medicament, such as a cell therapy medicament for intractable diseases.

The pharmaceutical composition according to one or more embodiments of the present invention can be used as a medicament for treating a disease selected from among immune-related disease, ischemic disease, lower limb ischemia, cerebral vascular ischemia, renal ischemia, pulmonary ischemia, neurological disease, graft-versus-host disease (GVHD), inflammatory bowel disease, Crohn's disease, ulcerative colitis, radiation enteritis, systemic erythematosus, lupus erythematosus, collagen disease, stroke, cerebral infarction, cerebral hematoma, cerebrovascular paralysis, cerebral tumor, cirrhosis, atopic dermatitis, multiple sclerosis, psoriasis, bullous epidermolysis, diabetes, mycosis fungoides (Alibert-Bazin syndrome), scleroderma, diseases resulting from degeneration and/or inflammation of connective tissues such as cartilage, articular cartilage defects, meniscal damage, osteochondrosis detachment, indestructible osteonecrosis, knee osteoarthritis, inflammatory arthritis, rheumatoid arthritis, eye disease, angiogenesis-related disease, ischemic heart disease, coronary heart disease, myocardial infarction, angina, heart failure, cardiomyopathy, valvular disease, wound, epithelial damage, fibrosis, pulmonary disease, muscular dystrophy, chronic pancreatitis, chronic nephritis, and cancer. The pharmaceutical composition according to one or more embodiments of the present invention may be administered in an amount that can exert therapeutic effects at a target site of treatment, so that the diseases mentioned above can be treated.

According to one or more embodiments of the present invention, the cell population comprising mesenchymal cells according to one or more embodiments of the present invention for use in a pharmaceutical composition is provided.

According to one or more embodiments of the present invention, the cell population comprising mesenchymal cells according to one or more embodiments of the present invention for use in a cell therapy medicament is provided.

According to one or more embodiments of the present invention, the cell population comprising mesenchymal cells according to one or more embodiments of the present invention for use in the treatment of the diseases is provided.

According to one or more embodiments of the present invention, the cell population comprising mesenchymal cells according to one or more embodiments of the present invention for administration to a patient or subject for regeneration of cardiac muscles, production of cardiomyocytes, angiogenesis, repair of blood vessels, or suppression of immune responses is provided.

According to one or more embodiments of the present invention, a method for transplanting cells into a patient or subject and a method for treatment of a disease in a patient or subject comprising a step of administering a therapeutically effective amount of the cell population comprising mesenchymal cells according to one or more embodiments of the present invention to the patient or subject are provided.

According to one or more embodiments of the present invention, use of the cell population comprising mesenchymal cells according to one or more embodiments of the present invention in the manufacture of a pharmaceutical composition is provided.

According to one or more embodiments of the present invention, use of the cell population comprising mesenchymal cells according to one or more embodiments of the present invention in the manufacture of a cell therapy medicament is provided.

According to one or more embodiments of the present invention, use of the cell population comprising mesenchymal cells according to one or more embodiments of the present invention in the manufacture of a medicament for treating the diseases is provided.

According to one or more embodiments of the present invention, use of the cell population comprising mesenchymal cells according to one or more embodiments of the present invention in the manufacture of a medicament that is administered to a patient or subject for regeneration of cardiac muscles, production of cardiomyocytes, angiogenesis, repair of blood vessels, or suppression of immune responses is provided.

A dose of the pharmaceutical composition according to one or more embodiments of the present invention is an amount of cells that can exert therapeutic effects on diseases when administered to a patient or a subject as compared with a patient or a subject to which the pharmaceutical composition has not been administered. A specific dose can be determined depending on a dosage form, an administration method, a purpose of use, and the age, body weight, and conditions of the patient or subject. A dose of the pharmaceutical composition is not particularly limited, and it is, for example, $10^4$ cells/kg of body weight or more, $10^5$ cells/kg of body weight or more, or $10^6$ cells/kg of body weight or more, in terms of the number of mesenchymal cells. While a dose is not particularly limited, for example, it is $10^9$ cells/kg of body weight or less in terms of the number of mesenchymal cells. The dose per one administration is preferably $10^{12}$ cells or less, more preferably $10^{11}$ cells or less, and further preferably $10^{10}$ cells or less, in terms of the number of mesenchymal cells.

A method for administering the pharmaceutical composition according to one or more embodiments of the present invention is not particularly limited. Examples thereof include subcutaneous injection, intralymphatic injection, intravenous injection, intraperitoneal injection, intrathoracic injection, direct injection into a focus, and direct transplantation into a focus.

The pharmaceutical composition according to one or more embodiments of the present invention can be used in the form of a preparation for injection for treatment of other diseases, a preparation for transplantation in the form of a cell aggregate or a sheet-like construct, or a gel preparation mixed with a gel. In a preferable embodiment of the present invention, as described above, the cell population can be detached from a substrate in the form of a cell sheet. Thus, the cell population obtained in the form of a cell sheet can be used as a preparation for transplantation of a sheet-like construct without processing (or with minimal processing). Specifically, a cell population comprising mesenchymal cells in the form of a cell sheet is an embodiment of the present invention.

The patient or subject targeted by the pharmaceutical composition according to one or more embodiments of the present invention is typically a human, and the patient or subject may be other animals. Examples of other animals include mammalian animals, such as dogs, cats, cattle, horses, pigs, sheep, monkeys, and ferrets, and birds, such as chickens.

The pharmaceutical composition according to one or more embodiments of the present invention can be stored in a frozen state until immediately before use. The pharmaceutical composition according to one or more embodiments of the present invention may contain any components used for treatment of humans. Examples of such components include, but are not limited to, salts, polysaccharides (e.g., HES and dextran), proteins (e.g., albumin), DMSO, and medium components (e.g., components contained in RPMI 1640 medium).

The pharmaceutical composition according to one or more embodiments of the present invention may comprise a cell population comprising mesenchymal cells diluted with an infusion preparation used as a pharmaceutically acceptable medium. The "infusion preparation (pharmaceutically acceptable medium)" used herein is not particularly limited, provided that it is a solution used for treatment of humans. Examples thereof include physiological saline, 5% dextrose, Ringer's solution, Ringer's lactate solution, Ringer's acetate solution, starting solution (Liquid No. 1), dehydration-supplementing solution (Liquid No. 2), maintenance infusion solution (No. 3 solution), and postoperative recovery solution (No. 4 solution.)

Other examples of diseases of a patient or subject that can be treated with the use of the cell population comprising mesenchymal cells, more specific examples of the diseases, and a specific procedure of treatment are described in, for example, Hare et al., J. Am. Coll. Cardiol., Dec. 8, 2009; 54 (24): 2277-2286; Honmou et al., Brain, 2011: 134, 1790-1807; Makhoul et al., Ann. Thorac. Surg., 2013; 95: 1827-1833; JP Patent No. 5950577, JP 2010-518096 A, JP 2012-509087 A, JP 2014-501249 A, JP 2013-256515 A, JP 2014-185173 A, JP 2010-535715 A, JP 2015-038059 A, JP 2015-110659 A, JP 2006-521121 A, JP 2009-542727 A, JP 2014-224117 A, JP 2015-061862 A, JP 2002-511094 A, JP 2004-507454 A, JP 2010-505764 A, JP 2011-514901 A, JP 2013-064003 A, and JP 2015-131795 A.

The present invention is described in greater detail with reference to the following examples, although the present invention is not limited to these examples.

EXAMPLES

Comparative Example 1

(Step 1-1: Collection of Amniotic Membrane)

The informed consent was obtained from a pregnant woman scheduled to undergo cesarean delivery (Donor #1), and fetal appendages, i.e., a fetal membrane and a placenta, were aseptically collected from Donor #1. The fetal membrane and the placenta obtained were placed in a sterile vat containing physiological saline, and the amniotic membrane was manually detached from the stump of the fetal membrane. The amniotic membrane was washed with the Hank's balanced salt solution (not containing Ca or Mg) to remove the adhered blood and blood clots.

(Step 1-2: Enzyme Treatment of Amniotic Membrane and Recovery of Mesenchymal Cells)

The amnion membrane comprising an epithelial cell layer and an extracellular matrix layer containing mesenchymal cells was immersed in the Hank's balanced salt solution (containing Ca and Mg) containing 240 PU/ml collagenase and 200 PU/ml Dispase I and subjected to shake stirring at 37° C. and 50 rpm for 90 minutes. Thus, the amniotic membrane was enzymatically treated. The solution after the enzyme treatment was filtrated through a nylon mesh with a mesh opening of 95 μm to remove the undigested amniotic membrane, and a cell suspension containing mesenchymal cells was recovered.

(Step 1-3: Culture of Mesenchymal Cells)

The cell populations comprising mesenchymal cells obtained in "Step 1-2: Enzyme treatment of amniotic membrane and recovery of mesenchymal cells" above were seeded in the CellStack® culture chamber (Corning). The seeding density was 6,000 cells/cm². After the cells were seeded, adhesion culture was performed until the cells became subconfluent in αMEM (alpha modification of Minimum Essential Medium Eagle) containing fetal bovine serum (FBS) (final concentration: 10%) and 10 ng/ml of a basic fibroblast growth factor (bFGF). After culture, 15 ml of TrypLE Select was added to each stack of CellStack®, and the cells were incubated at 37° C. for 3 minutes. After the incubation, approximately one-third of the cell populations remained adhered to the CellStack® culture chamber. The cells were incubated for an additional 5 minutes (8 minutes in total), the cell populations were completely detached from the culture chamber, and remaining cell populations were recovered. The cell populations obtained herein are at passage 0. Thereafter, one-fifth of the cell populations above were seeded in the CellStack® culture chamber as used in the previous culture and subjected to passage culture in αMEM containing FBS (final concentration: 10%) and 10 ng/ml of bFGF. The medium was replaced with a fresh medium once in 2 to 4 days. When the cells became subconfluent, 15 ml of TrypLE Select was added to each stack of CellStack®, and the cells were incubated at 37° C. for 3 minutes. After the incubation, approximately one-third of the cell populations remained adhered to the CellStack® culture chamber. The cells were incubated for an additional 5 minutes (8 minutes in total), the cell populations were completely detached from the culture chamber, and remaining cell populations were recovered. The cell populations obtained herein are at passage 1. Thereafter, RPMI 1640 was added to adjust the cell density to $2 \times 10^7$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to −80° C., followed by cryopreservation in liquid nitrogen for 1 day. Thereafter, the cryopreserved cell populations were thawed, the cell populations at passage 1 were seeded in CellStack® at the density of approximately 15,000 to 18,000 cells/cm², and adhesion culture was performed until the cells became subconfluent in αMEM (alpha modification of Minimum Essential Medium Eagle) containing fetal bovine serum (FBS) (final concentration: 10%) and 10 ng/ml of a basic fibroblast growth factor (bFGF). After culture, 15 ml of TrypLE Select was added to each stack of CellStack®, and the cells were incubated at 37° C. for 3 minutes. After the incubation, approximately one-third of the cell populations remained adhered to the CellStack® culture chamber. The cells were incubated for an additional 5 minutes (8 minutes in total), the cell populations were completely detached from the culture chamber, and remaining cell populations were recovered. The cell populations obtained herein are at passage 2. Thereafter, one-fifth of the cell populations above were seeded in the CellStack® culture chamber as used in the previous culture and subjected to passage culture in αMEM containing FBS (final concentration: 10%) and 10 ng/ml of bFGF. The medium was replaced with a fresh medium once in 2 to 4 days. When the cells became subconfluent, 15 ml of TrypLE Select was added to each stack of CellStack®, and the cells were incubated at 37° C. for 3 minutes. After the incubation, approximately one-third of the cell populations remained adhered to the CellStack® culture chamber. The cells were incubated for an additional 5 minutes (8 minutes in total), the cell populations were completely detached from the culture chamber, and remaining cell populations were recovered. The cell populations obtained herein are at passage 3. To the cell populations, RPMI 1640 was added to adjust the cell density to $4 \times 10^6$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to −80° C., followed by cryopreservation in liquid nitrogen for 1 day. Thereafter, the cryopreserved cell populations were thawed, the cell populations at passage 3 were seeded in CellStack® at the density of approximately 6,000 cells/cm², and adhesion culture was performed until the cells became subconfluent in αMEM (alpha modification of Minimum Essential Medium Eagle) containing fetal bovine serum (FBS) (final concentration: 10%) and 10 ng/ml of a basic fibroblast growth factor (bFGF). After culture, 15 ml of TrypLE Select was added to each stack of CellStack®, and the cells were incubated at 37° C. for 3 minutes. After the incubation, approximately one-third of the cell populations remained adhered to the CellStack® culture chamber. The cells were incubated for an additional 5 minutes (8 minutes in total), the cell populations were completely detached from the culture chamber, and remaining cell populations were recovered. The cell populations obtained herein are at passage 4. Thereafter, one-fifth of the cell populations above were seeded in the CellStack® culture chamber as used in the previous culture and subjected to passage culture in αMEM containing FBS (final concentration: 10%) and 10 ng/ml of bFGF. The medium was replaced with a fresh medium once in 2 to 4 days. When the cells became subconfluent, 15 ml of TrypLE Select was added to each stack of CellStack®, and the cells were incubated at 37° C. for 3 minutes. After the incubation, approximately one-third of the cell populations remained adhered to the CellStack® culture chamber. The cells were incubated for an additional 5 minutes (8 minutes in total), the cell populations were completely detached from the culture chamber, and remaining cell populations were recovered. The cell populations obtained herein are at passage 5. Thereafter, RMPI 1640 was added to adjust the cell density to $4 \times 10^6$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to −80° C., followed by cryopreservation in liquid nitrogen.

(Step 1-4: Surface Antigen Analysis of Mesenchymal Cells)

The cell populations at passage 5 cultured in the manner described above were analyzed using a flow cytometer concerning various surface antigens (CD324 positive rate, CD73 positive rate, CD90 positive rate, CD105 positive rate, CD166 positive rate, CD45 negative rate, CD326 negative rate). As a result, the CD324 positive rate was found to be less than 70% (i.e., 33%), the CD105 positive rate was found to be 70% or more (i.e., 93%), and the CD73, CD90, and CD166 positive rates were found to be 90% or more (i.e., CD73 positive rate: 99%; CD90 positive rate:

93%; CD166 positive rate: 97%). The CD45 and CD326 negative rates were found to be 95% or more (i.e., CD45 negative rate: 100%; CD326 negative rate: 100%). The results indicate that the cell populations cultured in the manner described above comprise mesenchymal cells. The results also indicate that the cell populations at passage 5 of Comparative Example 1 satisfy the condition that the proportion of mesenchymal cells that are positive for CD90 is 90% or more but do not satisfy the condition that the proportion of cells that are positive for CD324 is 70% or more.

In the measurement, REA Control Antibody (S) APC (Miltenyi Biotec, Clone: REA293; Model: 130-113-434) was used as the isotype control antibody, the APC anti-human CD324 antibody (Miltenyi Biotec, Clone: REA811; Model: 130-111-840) was used as the antibody targeting the CD324 antigen, the APC anti-human CD73 antibody (Miltenyi Biotec, Clone: REA804; Model: 130-111-909) was used as the antibody targeting the CD73 antigen, the APC anti-human CD90 antibody (Miltenyi Biotec, Clone: REA897; Model: 130-114-861) was used as the antibody targeting the CD90 antigen, the APC anti-human CD105 antibody (Miltenyi Biotec, Clone: REA794; Model: 130-112-166) was used as the antibody targeting the CD105 antigen, the APC anti-human CD166 antibody (Miltenyi Biotec, Clone: REA442; Model: 130-106-576) was used as the antibody targeting the CD166 antigen, the APC anti-human CD45 antibody (Miltenyi Biotec, Clone: REA747; Model: 130-110-633) was used as the antibody targeting the CD45 antigen, and the APC anti-human CD326 antibody (Miltenyi Biotec, Clone: REA764; Model: 130-111-000) was used as the antibody targeting the CD326 antigen. Surface antigen analysis was performed using Guava easyCyte (Merck) by subjecting 30,000 cells to analysis and designating the flow rate at 35.4 μl/min. The proportion of cells positive for each antigen (i.e., the positive rate) was determined in the manner described below.

(1) The results of measurement of the isotype control are dot-plotted as SSC on the vertical axis and as FSC on the horizontal axis.

(2) The cell population corresponding to mesenchymal cells is gated, and the cell population is shown in a histogram showing the cell number on the vertical axis and the fluorescence intensity of APC on the horizontal axis.

(3) In the histogram of (2), all regions (gates) in which the proportion of a cell population exhibiting higher fluorescence intensity is 0.5% or less in the total number of cells measured using the isotype control antibody are selected.

(4) The proportion of cells contained in the gate selected in (3) in the total number of cells measured using the antibody reacting with the surface antigen marker is determined.

Example 1

(Step 2-1: Collection of Amniotic Membrane)

An amniotic membrane was obtained from the same donor as in Comparative Example 1 (Donor #1) in the same manner as in Comparative Example 1.

(Step 2-2: Enzyme Treatment of Amniotic Membrane and Recovery of Mesenchymal Cells)

A cell population comprising mesenchymal cells was obtained in the same manner as in Comparative Example 1.

(Step 2-3: Culture of Mesenchymal Cells)

The cell populations comprising mesenchymal cells obtained in "Step 1-2: Enzyme treatment of amniotic membrane and recovery of mesenchymal cells" above were seeded in the CellStack® culture chamber (Corning). The seeding density was 6,000 cells/cm². After the cells were seeded, adhesion culture was performed until the cells became subconfluent in αMEM containing the human platelet lysate (hPL) (final concentration: 5%). After culture, 15 ml of TrypLE Select was added to each stack of CellStack®, the cells were incubated at 37° C. for 3 minutes, and the cell populations were completely detached. The cell populations obtained herein are at passage 0. Thereafter, one-fifth of the cell populations above were seeded in the CellStack® culture chamber as used in the previous culture and subjected to passage culture in αMEM containing hPL (final concentration: 5%). The medium was replaced with a fresh medium once in 2 to 4 days. When the cells became subconfluent, 15 ml of TrypLE Select was added to each stack of CellStack®, the cells were incubated at 37° C. for 3 minutes, and the cell populations were completely detached. The cell populations obtained herein are at passage 1. Thereafter, RPMI 1640 was added to adjust the cell density to $2 \times 10^7$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to −80° C., followed by cryopreservation in liquid nitrogen for 1 day. Thereafter, the cryopreserved cell populations were thawed, the cell populations at passage 1 were seeded in CellStack® at the density of approximately 15,000 to 18,000 cells/cm², and adhesion culture was performed until the cells became subconfluent in αMEM containing the human platelet lysate (hPL) (final concentration: 5%). Thereafter, 15 ml of TrypLE Select was added to each stack of CellStack®, the cells were incubated at 37° C. for 3 minutes, and the cell populations were completely detached. The cell populations obtained herein are at passage 2. Subsequently, one-fifth of the cell populations above were seeded in the CellStack® culture chamber as used in the previous culture and subjected to passage culture in αMEM containing hPL (final concentration: 5%). The medium was replaced with a fresh medium once in 2 to 4 days. When the cells became subconfluent, 15 ml of TrypLE Select was added to each stack of CellStack®, the cells were incubated at 37° C. for 3 minutes, and the cell populations were completely detached. The cell populations obtained herein are at passage 3. Thereafter, RPMI 1640 was added to adjust the cell density to $4 \times 10^6$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to −80° C., followed by cryopreservation in liquid nitrogen for 1 day. Thereafter, the cryopreserved cell populations were thawed, the cell populations at passage 3 were seeded in CellStack® at the density of approximately 6,000 cells/cm², and adhesion culture was performed until the cells became subconfluent in αMEM containing the human platelet lysate (hPL) (final concentration: 5%). Thereafter, 15 ml of TrypLE Select was added to each stack of CellStack®, the cells were incubated at 37° C. for 3 minutes, and the cell populations were completely detached. The cell populations obtained herein are at passage 4. Subsequently, one-fifth of the cell populations above were seeded in the CellStack® culture chamber as used in the previous culture and subjected to passage culture in αMEM containing hPL (final concentration: 5%). The medium was replaced with a fresh medium once in 2 to 4 days. When the cells became subconfluent, 15 ml of TrypLE Select was added to each stack of CellStack®, the cells were incubated at 37° C. for 3 minutes, and the cell populations were completely detached. The cell populations obtained herein are at passage 5. To the cell populations, RPMI 1640 was added to adjust the cell density to $4 \times 10^6$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to −80° C., followed by cryo-preservation in liquid nitrogen.

(Step 2-4: Surface Antigen Analysis of Mesenchymal Cells)

The cell populations at passage 5 cultured in the manner described above were analyzed using a flow cytometer concerning various surface antigens (CD324 positive rate, CD73 (known as an MSC marker) positive rate, CD90 positive rate, CD105 positive rate, CD166 positive rate, CD45 negative rate, CD326 negative rate). As a result, the CD324 and CD105 positive rates were found to be 70% or more (i.e., CD324 positive rate: 91%; CD105 positive rate: 95%), and the CD73, CD90, and CD166 positive rates were found to be 90% or more (i.e., CD73 positive rate: 100%; CD90 positive rate: 100%; CD166 positive rate: 99%). The CD45 and CD326 negative rates were found to be 95% or more (i.e., CD45 negative rate: 100%; CD326 negative rate: 99%). The results indicate that the cell populations cultured in the manner described above comprise mesenchymal cells. The results also indicate that, in the cell populations described in Example 1, the proportion of cells that are positive for CD324 is 70% or more and the proportion of mesenchymal cells that are positive for CD90 is 90% or more.

The methods and the reagents used herein are the same as those used in Comparative Example 1.

Example 2

In Example 2 below, cell populations comprising mesenchymal cells were obtained from donors under enzyme treatment conditions and culture conditions different from those employed in Comparative Example 1 and Example 1.

The informed consent was obtained from 3 pregnant women scheduled to undergo cesarean delivery (Donors #2 to #4) who were different from the donor in Comparative Example 1 and Example 1, and fetal appendages, i.e., fetal membranes and placenta, were aseptically collected from Donors #2 to #4.

(Step 3-1: Collection of Amniotic Membrane)

Amniotic membranes were obtained in the same manner as in Comparative Example 1 and Example 1.

(Step 3-2: Enzyme Treatment of Amniotic Membrane and Recovery of Mesenchymal Cells)

The amnion membrane comprising an epithelial cell layer and an extracellular matrix layer containing mesenchymal cells was immersed in the Hank's balanced salt solution (containing Ca and Mg) containing 480 PU/ml collagenase and 400 PU/ml Dispase I and subjected to shake stirring at 37° C. and 50 rpm for 90 minutes. Thus, the amniotic membranes were enzymatically treated. The solution after the enzyme treatment was filtrated through a nylon mesh with a mesh opening of 95 μm to remove undigested amniotic membrane, and a cell suspension containing mes-enchymal cells was recovered.

(Step 3-3: Culture of Mesenchymal Cells)

The cell populations comprising mesenchymal cells obtained in "Step 3-2: Enzyme treatment of amniotic mem-brane and recovery of mesenchymal cells" above were seeded in the CellStack® culture chamber. The seeding density was 1,000 cells/cm². After the cells were seeded, adhesion culture was performed until the cells became subconfluent in αMEM containing the human platelet lysate (hPL) (final concentration: 5%). The medium was replaced with a fresh medium once in 3 to 5 days. After culture, 15 ml of TrypLE Select was added to each stack of CellStack®, the cells were incubated at 37° C. for 3 minutes, and the cell populations were completely detached. The cell populations obtained herein are at passage 0. Thereafter, physiological saline was added to adjust the cell density to $2 \times 10^7$ cells/ml. An equivalent amount of a CP-1® solution (a mixture of CP-1® and 25% human serum albumin (34:16)) was added thereto, 1 ml each of the mixture was transferred to cryovi-als, and the resultant was slowly frozen to −80° C., followed by cryopreservation in liquid nitrogen for 1 day. Thereafter, the cryopreserved cell populations were thawed, the cell populations at passage 1 were seeded in CellStack® at the density of approximately 1,000 cells/cm², and adhesion culture was performed for 5 days until the cells became subconfluent in αMEM containing the human platelet lysate (hPL) (final concentration: 5%). Thereafter, 15 ml of TrypLE Select was added to each stack of CellStack®, the cells were incubated at 37° C. for 3 minutes, and the cell populations were completely detached. The cell populations obtained herein are at passage 1. Subsequently, physiologi-cal saline was added to adjust the cell density to $2 \times 10^7$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to −80° C., followed by cryopreservation in liquid nitrogen for 1 day. Thereafter, the cryopreserved cell populations were thawed, the cell populations at passage 2 were seeded in CellStack® at the density of approximately 1,000 cells/cm², and adhe-sion culture was performed for 5 days until the cells became subconfluent in αMEM containing the human platelet lysate (hPL) (final concentration: 5%). Thereafter, 15 ml of TrypLE Select was added to each stack of CellStack®, the cells were incubated at 37° C. for 3 minutes, and the cell populations were completely detached. The cell populations obtained herein are at passage 2. To the cell populations, physiological saline was added to adjust the cell density to $4 \times 10^6$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to −80° C., followed by cryopreservation in liquid nitrogen.

(Step 3-7: Surface Antigen Analysis of Mesenchymal Cells)

The cell populations at passage 2 cultured in the manner described in Step 3-3 (#2 to #4) were analyzed using a flow cytometer concerning various surface antigens (CD324 positive rate, CD73 positive rate, CD90 positive rate, CD105 positive rate, CD166 positive rate, CD45 negative rate, CD326 negative rate). As a result, the CD324 and CD105 positive rates were found to be 70% or more (i.e., #2: CD324 positive rate: 90%; CD105 positive rate: 89%; #3: CD324 positive rate: 87%; CD105 positive rate: 91%; and #4: CD324 positive rate: 87%; CD105 positive rate: 74%), and the CD73, CD90, and CD166 positive rates were found to be 90% or more (i.e., #2: CD73 positive rate: 100%; CD90 positive rate: 100%; CD166 positive rate: 99%; #3: CD73 positive rate: 99%; CD90 positive rate: 99%; CD166 positive rate: 97%; and #4: CD73 positive rate: 100; CD90 positive rate: 100%; CD166 positive rate: 98%). The CD45 and CD326 negative rates were found to be 95% or more (i.e., #2: CD45 negative rate: 99%; CD326 negative rate: 99%; #3: CD45 negative rate: 100%; CD326 negative rate:

100%; #4: CD45 negative rate: 100%; CD326 negative rate: 100%). The results indicate that all the cell populations #2, #3, and #4 cultured in the manner described above comprise cells that are positive for CD324. The results also indicate that, in the cell populations described in Example 2, the proportion of cells that are positive for CD324 is 70% or more and the proportion of mesenchymal cells that are positive for CD90 is 90% or more. The methods and the reagents used herein are the same as those used in Comparative Example 1.

<Evaluation Experiment: Evaluation of Detachability of Mesenchymal Cells from Culture Substrate>

(Evaluation 1: Evaluation of the Cell Population Obtained in Comparative Example 1)

The cell population at passage 5 cultured in the manner described in Step 1-3 of Comparative Example 1 (#1) was thawed, the cell population at passage 5 was seeded on a 6-well plate at the density of approximately 10,000 cells/cm$^2$, and adhesion culture was initiated in $\alpha$MEM (alpha modification of Minimum Essential Medium Eagle) containing fetal bovine serum (FBS) (final concentration: 10%) and 10 ng/ml of a basic fibroblast growth factor (bFGF). The medium was replaced with a fresh medium once in 3 to 5 days. While the degree of confluency reached 100% 5 days after the initiation of culture, culture was continued without performing detachment treatment. Cell configurations were observed under a phase contrast microscope (Olympus) 4, 5, 6, 7, 10, 11, 12, 13, 14, 17, and 21 days after the initiation of culture. Cells reached overconfluency 7 days after the initiation of culture, and cells were adhered to each other without gaps. However, no apparent change was observed in cell configurations thereafter, and cells were not spontaneously detached from the 6-well plate 21 days after the initiation of culture (FIG. 1: cells 21 days after the initiation of culture).

(Evaluation 2: Evaluation of Cell Populations Obtained in Examples 1 and 2)

Figure 2:
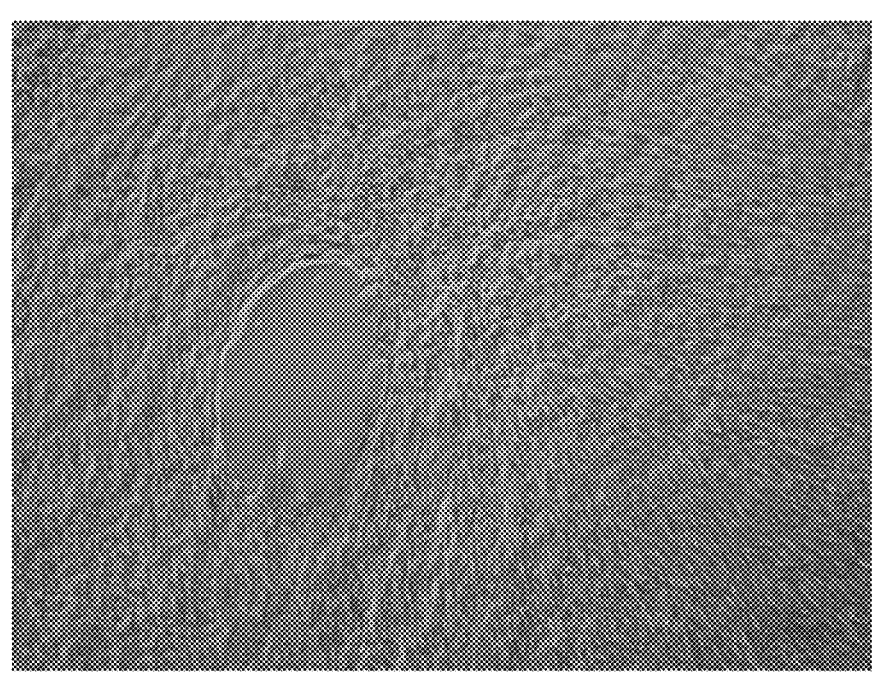
FIG. 2 shows an image of cells 10 days after initiation of the 5th passage culture of the cell population of Example 2 prepared from Donor #1 observed in Evaluation 2 (magnification: 40). Detachment of some cells was observed.
Figure 3:
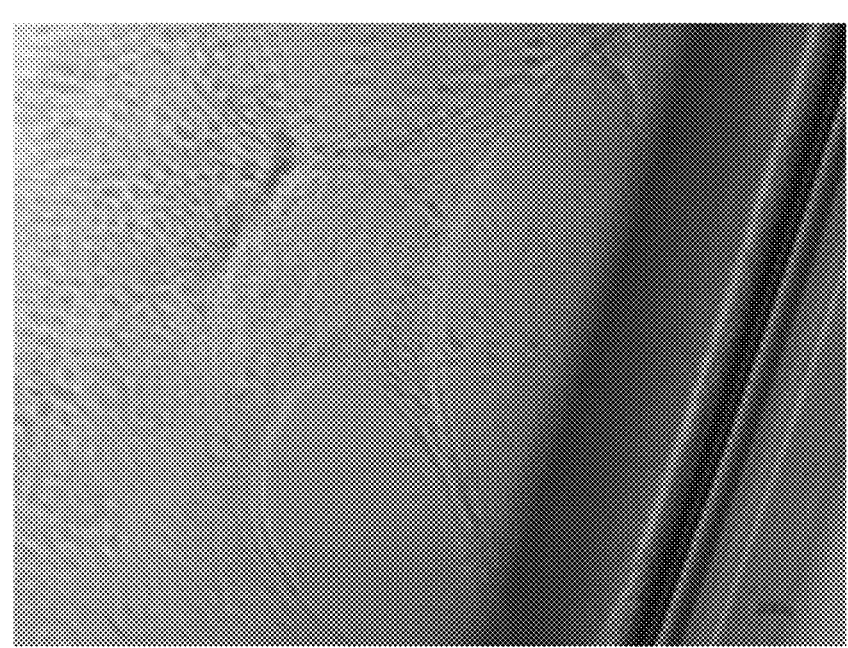
FIG. 3 shows an image of cells 10 days after initiation of the 2nd passage culture of the cell population of Example 1 prepared from Donor #3 observed in Evaluation 2 (magnification: 100). Detachment of some cells was observed.
Figure 4:
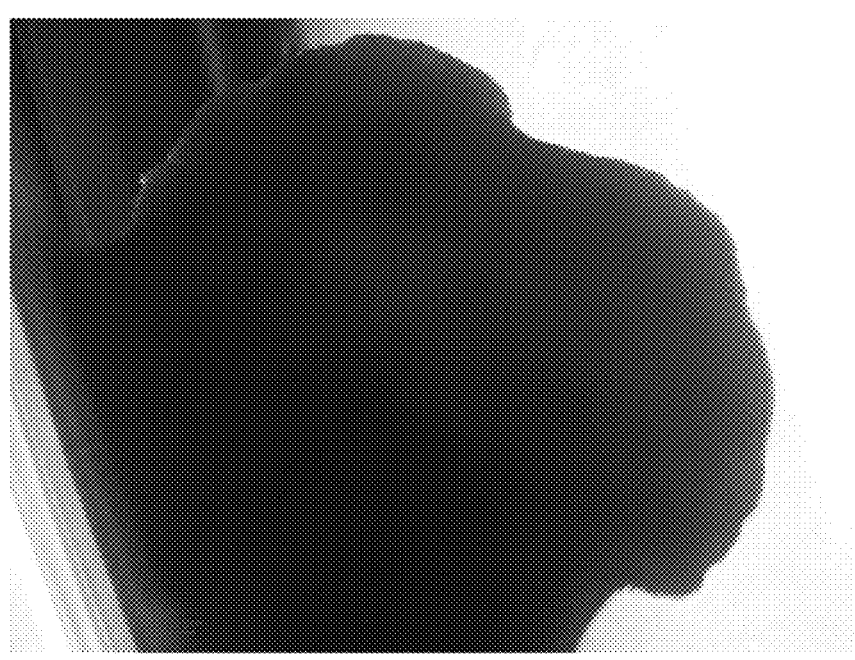
FIG. 4 shows an image of cells 11 days after initiation of the 2nd passage culture of the cell population of Example 2 prepared from Donor #3 observed in Evaluation 2 (magnification: 40). A mass structure (a cell aggregate) formed as a result of shrinkage of the cell sheet detached from the substrate was observed.

The cell population at passage 5 cultured in the manner described in Step 2-3 of Example 1 (#1) and the cell population at passage 2 cultured in the manner described in Step 3-3 of Example 2 (#3) were thawed, the cells were seeded in a culture vessel (a 6-well plate) at the density of approximately 10,000 cells/cm$^2$, and adhesion culture was initiated in $\alpha$MEM containing the human platelet lysate (hPL) (final concentration: 5%). The medium was replaced with a fresh medium once in 3 to 5 days. While the degree of confluency reached 100% 4 days after the initiation of culture, culture was continued without performing detachment treatment. Cells were observed under a phase contrast microscope (Olympus) 4, 5, 6, 7, 10, 11, 12, 13, 14, 17, and 21 days after the initiation of culture. Cells reached overconfluency 5 days after the initiation of culture, cells were adhered to each other without gaps, and some cells were superposed on top of one another. Some of the cell populations was spontaneously detached from the culture vessel 10 days after the initiation of culture (FIGS. 2 and 3: partial cell detachment observed 10 days after the initiation of culture). Some of the detached cell populations was in the form of sheets. The entire cell populations were spontaneously detached from the culture vessel 11 days after the initiation of culture, and cell sheets were formed (FIG. 4: a mass structure formed as a result of shrinkage of a detached cell sheet, which is observed 11 days after the initiation of culture of the cell populations at passage 2 of Example 2 prepared from Donor #3).

The results indicate that a cell population in which the proportion of cells that are positive for CD324 is 70% or more and the proportion of mesenchymal cells that are positive for CD90 is 90% or more is spontaneously detached from the culture vessel. A cultured cell population that satisfies the conditions described above can be easily recovered without chemical means, such as addition of a removal agent, or physical means, such as recovery of a cell population with the use of a cell scraper. Thus, the cell population according to the present invention does not require the step of detachment, which was necessary according to a conventional technique, and damages imposed on cells can be reduced or suppressed.

A cell population in which the proportion of cells that are positive for CD324 is 70% or more and the proportion of mesenchymal cells that are positive for CD90 is 90% or more can be obtained in the form of a cell sheet after it is detached from a culture vessel. According to the method of the present invention, specifically, the chemical or physical means as described above or any special treatment on a culture vessel is not necessary to prepare a cell sheet. A cell sheet is a form suitable for clinical applications from the viewpoint of operability and it is thus useful.

<Preparation of Pharmaceutical Composition>

The cell populations comprising mesenchymal cells obtained in Example 2 (#2 to #4) are partially subjected to preparation of a pharmaceutical composition. A pharmaceutical composition containing $2.0 \times 10^8$ mesenchymal cells, 6.8 ml of a CP-1® solution, 3.2 ml of a 25% human serum albumin solution, and 10 ml of physiological saline is prepared (a cell preparation). The pharmaceutical composition is sealed in a freezing bag and stored in a frozen state. The pharmaceutical composition can be thawed at the time of use and provided to a patient.

<Summary of Negative Rates and Positive Rates for Surface Antigen>

Table 1 shows a summary of the results of surface antigen analysis, periods of enzyme treatment at the time of passage, and the capacity for cell sheet formation in Comparative Example 1, Example 1, and Example 2.

TABLE 1

|  | Comparative Example 1 | Example 1 | Example 2 | | |
|---|---|---|---|---|---|
|  | #1 | #1 | #2 | #3 | #4 |
| CD324 positive rate | 33% | 91% | 90% | 87% | 87% |
| CD73 positive rate | 99% | 100% | 100% | 99% | 100% |
| CD90 positive rate | 93% | 100% | 100% | 99% | 100% |
| CD105 positive rate | 93% | 95% | 89% | 91% | 74% |
| CD166 positive rate | 97% | 99% | 99% | 97% | 98% |
| CD45 negative rate | 100% | 100% | 99% | 100% | 100% |
| CD326 negative rate | 100% | 99% | 99% | 100% | 100% |
| Period of treatment with TrypLE Select at the time of cell detachment (passage) | 8 min | 3 min | 3 min | 3 min | 3 min |
| Cell detachability from culture substrate (H: high; L: low) | L | H | H | H | H |
| Capacity for cell sheet formation | Not capable | Capable | — | Capable | — |

Reference Example (Step 4-1: Culture of Bone Marrow-Derived Mesenchymal Stem Cells)

Human bone marrow-derived mesenchymal stem cells (hMSCs, Lonza) were purchased, thawed, seeded in a dish ($\varphi$15 cm) at the density of 6,000 cells/cm$^2$, and subjected to adhesion culture to subconfluency in a dedicated-purpose medium (Lonza). The medium was replaced with a fresh medium once in 3 to 5 days. Thereafter, a cell population was detached using TrypLE Select, and physiological saline was added to adjust the cell density to 2×10$^6$ cells/ml. An equivalent amount of a CP-1® solution (a mixture of CP-1® and 25% human serum albumin (34:16)) was added thereto, 1 ml each of the mixture was transferred to cryovials, and the resultant was slowly frozen to –80° C., followed by cryo-preservation in liquid nitrogen.

(Step 4-2: Surface Antigens Analysis of Bone Marrow-Derived Mesenchymal Stem Cells)

The cell population comprising bone marrow-derived mesenchymal stem cells cultured in the manner described in Step 4-1 was analyzed using a flow cytometer concerning various surface antigens (CD324 positive rate, CD73 (known as an MSC marker) positive rate, CD90 positive rate, CD105 positive rate, CD166 positive rate, CD45 negative rate, CD326 negative rate). As a result, the CD324 positive rate was found to be 70% or less (i.e., 1%), and the CD73, CD90, CD105, and CD166 positive rates were found to be 90% or more (i.e., CD73 positive rate: 97%; CD90 positive rate: 98%; CD105 positive rate: 97%; CD166 positive rate: 95%). The CD45 and CD326 negative rates were found to be 95% or more (i.e., CD45 negative rate: 100%; CCD326 negative rate: 100%).

All publications, patents, and patent applications cited herein are incorporated herein by reference in their entirety.

The invention claimed is:

1. A method for producing a cell population comprising mesenchymal cells comprising:

a step of culturing a cell population comprising mesenchymal cells derived from a fetal appendage to obtain a cultured cell population;

subculturing said cultured cell population in a culture medium which contains an effective amount of human platelet lysate which does not contain fetal bovine serum to produce a subcultured cell population; and a step of selecting a subcultured cell population having the properties (a), (b), and (c) below from among the cell populations comprising mesenchymal cells:

(a) a cell population in which the proportion of cells positive for CD324 is 80% or more;

(b) a cell population in which the proportion of mesenchymal cells positive for CD90 is 90% or more;

(c) a cell population in which the proportion of mesenchymal cells positive for CD326 is 5% or less; and wherein the medium in said subculturing contains 3% to 20% by weight of human platelet lysate.

2. The method of claim 1, wherein the fetal appendage is an amniotic membrane.

* * * * *